(12) United States Patent
Schurzig et al.

(10) Patent No.: US 10,994,128 B2
(45) Date of Patent: May 4, 2021

(54) FIXATION COMPONENT FOR INSERTION TOOLS FOR MINIMALLY INVASIVE COCHLEAR IMPLANTS

(71) Applicant: MED-EL Elektromedizinische Geraete GmbH, Innsbruck (AT)

(72) Inventors: Daniel Schurzig, Hannover (DE); Max Frölich, Hannover (DE)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 283 days.

(21) Appl. No.: 16/328,148

(22) PCT Filed: Oct. 23, 2017

(86) PCT No.: PCT/US2017/057792
§ 371 (c)(1),
(2) Date: Feb. 25, 2019

(87) PCT Pub. No.: WO2018/080955
PCT Pub. Date: May 3, 2018

(65) Prior Publication Data
US 2019/0184155 A1  Jun. 20, 2019

Related U.S. Application Data

(60) Provisional application No. 62/411,713, filed on Oct. 24, 2016.

(51) Int. Cl.
*A61N 1/05* (2006.01)
*A61N 1/36* (2006.01)
*A61B 17/34* (2006.01)
*A61N 1/375* (2006.01)

(52) U.S. Cl.
CPC ....... *A61N 1/0541* (2013.01); *A61N 1/36038* (2017.08); *A61B 17/3468* (2013.01); *A61N 1/3752* (2013.01)

(58) Field of Classification Search
CPC .................................................. A61B 17/3468
See application file for complete search history.

(56) References Cited

U.S. PATENT DOCUMENTS

| | | | |
|---|---|---|---|
| 2008/0234793 A1* | 9/2008 | Gibson | A61N 1/0541 607/137 |
| 2012/0185028 A1* | 7/2012 | Gantz | A61N 1/0541 607/137 |
| 2015/0224300 A1* | 8/2015 | Hagr | A61N 1/0541 607/137 |

* cited by examiner

*Primary Examiner* — Scott Luan
(74) *Attorney, Agent, or Firm* — Sunstein LLP

(57) ABSTRACT

An implantable electrode arrangement for a cochlear implant system is described. A retraction limiter fits around and securely engages a portion of the distal end of an electrode lead. The retraction limiter includes flexible retraction limiting projections longitudinally distributed along its outer surface. An insertion tube fits around the electrode array and the retraction limiter and engages against the outer surface of the patient cochlea at a cochlear opening. An insertion plunger fits within the insertion tube and engages against the proximal end of the retraction limiter. The insertion plunger slides within the insertion tube to push against the proximal end of the retraction limiter to push the electrode array through the cochlear opening into the patient cochlea.

9 Claims, 7 Drawing Sheets

FIXATION COMPONENT FOR INSERTION TOOLS FOR MINIMALLY INVASIVE COCHLEAR IMPLANTS

CROSS-REFERENCE TO RELATED APPLICATIONS

This application is a 371 national phase entry of Patent Cooperation Treaty Application PCT/US2017/057792, filed Oct. 23, 2017, which in turn claims priority from U.S. Provisional Patent Application 62/411,713, filed Oct. 24, 2016, both of which are incorporated herein by reference in their entireties.

TECHNICAL FIELD

The present invention relates to medical implants, and more specifically to an implantable electrode arrangement for cochlear implant systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolus where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by an auditory prosthesis system such as a cochlear implant that electrically stimulates auditory nerve tissue with small currents delivered by multiple stimulation contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through an electrode lead 109 to an implanted electrode array 110 which penetrates into the cochlea 104 through a surgical opening in the outer surface of the cochlea 104. Typically, this electrode array 110 includes multiple stimulation contacts 112 on its surface that deliver the stimulation signals to adjacent neural tissue of the cochlea 104 which the brain of the patient interprets as sound. The individual stimulation contacts 112 may be activated sequentially or simultaneously in one or more contact groups.

Cochlear implantation is a major surgery that involves full anesthesia and usually takes from 1.5 to 5 hours. A significant portion of that time is required for the labor intensive mastoidectomy in which the surgeon creates an opening in the outer mastoid bone of the skull and a bore path through that bone and the middle ear to gain access to the cochlea prior to implantation. During this process, the surgeon needs to carefully mill down through the mastoid bone to the cochlea starting right behind the ipsilateral ear, and using anatomical landmarks to find his way. One of these landmarks is the facial nerve which, if damaged or cut, may cause facial paralysis of the patient. Aiming at the reduction of surgery time, patient stress, and risk of accidents such as facial nerve damage, there are research attempts to perform cochlear implantation using image guidance using preoperative CT images for the determination of a single bore path from behind the ear down to the point on the outer surface of the cochlea through which the implant electrode array needs to be inserted.

These methods are described in detail, for example, in Labadie et al. "Minimally invasive, image-guided, facial-recess approach to the middle ear: demonstration of the concept of percutaneous cochlear access in vitro." *Otology & Neurotology* 26.4 (2005): 557-562; which is incorporated herein by reference. While these attempts are known to be very beneficial in terms of the severity of the surgery, the actual insertion of the electrode array into the cochlea becomes significantly more difficult—the geometrical boundary conditions do not allow for visual access of the cochlea opening, and there is little or no space available for surgical insertion mechanisms.

FIG. 2A shows structural details of a cochlear implant electrode arrangement at the electrode opening 201 into the implanted cochlea 104. After the insertion procedure, the electrode array 110 in this example tends to lie toward the outer lateral wall of the spiral-shaped cochlea 104. Over time, there can be a tendency for the electrode array to spring back and retract back out through the electrode opening 201, as shown in FIG. 2B. The degree of spring back varies depending among other factors on how deeply the electrode array 110 is inserted into the cochlea 104, how well the electrode opening 201 is packed with fascia material, and the specific geometry at the electrode opening 201.

Such post-surgical electrode retraction pulls the nearest stimulation contact 112 away from its intended target neural tissue within the cochlea 104 back toward the electrode opening 201, or even further, back outside the cochlea 104 into the middle ear 104. This can produce pain sensation in the patient when that stimulation contact 112 is energized. Usually in such circumstances, that stimulation contact 112 will be inactivated and fewer stimulation contacts 112 remain for use to produce sound sensation. In some cases even revision surgery may be required, see for example Connell, S. S., Balkany, T. J., Hodges, A. V., Telischi, F. F., Angeli, S. I., Eshraghi, A. A. in "Electrode migration after cochlear Implantation" published in Otology & Neurotology, 2008 No. 29: 156-159.

Various approaches have been attempted to resist such post-surgical retraction. A cork-shaped stopper has been used to tightly wedge the electrode lead in the electrode opening. An anti-retraction skirt has been implemented on the electrode array at the electrode opening which is made of polymer material that swells when contacted by the liquid preilymph medium, thereby holding the electrode array in place. Some electrode arrays have a permanent pre-curved shape that does not relax or spring back after insertion into the cochlea. Other electrode arrangements contain an internal malleable material on either side of the electrode opening which maintains a bent shape after full insertion of the electrode array to resist retraction. A surgical group in Hannover Germany has added to the implant electrode a wing of flexible silicone material that can be fixed to a groove in the bony material on the outer surface of the cochlea near the electrode opening. All of these efforts have suffered from various issues that leave each an imperfect solution.

SUMMARY

Embodiments of the present invention are directed to an implantable electrode arrangement for a cochlear implant system that prevents post-surgical retraction. An extracochlear electrode lead is configured for carrying one or more cochlear stimulation signals from a proximal end of the electrode lead at a mastoid opening in a patient mastoid bone into the middle ear to a distal end of the electrode lead at a cochlear opening in the outer surface of a patient cochlea. An intracochlear electrode array is configured for insertion through the cochlear opening into the patient cochlea. The electrode array has a proximal end connected to the distal end of the electrode lead, and an outer surface with stimulation contacts configured for applying the cochlear stimulation signals to target neural tissue within the patient cochlea. An insertion mechanism includes a retraction limiter configured to fit around and securely engage a portion of the distal end of the electrode lead. The retraction limiter has flexible retraction limiting projections longitudinally distributed along its outer surface between the proximal end of the retraction limiter and the distal end of the retraction limiter. An insertion tube is configured to fit around the electrode array and the retraction limiter and engages against the outer surface of the patient cochlea at the cochlear opening. An insertion plunger is configured to fit within the insertion tube and engage against the proximal end of the retraction limiter. The insertion mechanism is operable for the insertion plunger to slide within the insertion tube to push against the proximal end of the retraction limiter to push the electrode array through the cochlear opening into the patient cochlea, and at least a portion of the retraction limiter through the mastoid opening into the middle ear so that when the insertion tube is withdrawn back through the mastoid opening, one or more of the retraction limiting projections enters into the middle ear and displaces out away from the outer surface of the retraction limiter and blocks the mastoid opening so as to prevent retraction of the electrode lead back out from the middle ear.

In further specific embodiments, the retraction limiter may comprise multiple compressible elliptical segments configured to be compressed radially inward to fit within the insertion tube, and configured to expand radially outward when the insertion tube is withdrawn back through the mastoid opening to form the retraction limiting projections. Or the retracting limiting projections may be opposing pairs of flexible flaps.

Embodiments of the present invention also include a method of implanting an electrode array in a patient cochlea. A bore hole is prepared including a mastoid opening through a patient mastoid bone into the middle ear and a cochlear opening through an outer surface of a patient cochlea into the cochlea. A retraction limiter is securely fit around a distal end of an electrode lead that is configured for carrying one or more cochlear stimulation signals. The retraction limiter has a proximal end, a distal end, an outer surface, and a plurality of flexible retraction limiting projections longitudinally distributed along the outer surface of the retraction limiter between the proximal end of the retraction limiter and the distal end of the retraction limiter. An insertion tube is fit around the retraction limiter and an electrode array that has a proximal end connected to the distal end of the electrode lead and an outer surface with a plurality of stimulation contacts configured for applying the cochlear stimulation signals to target neural tissue within an implanted patient cochlea. An insertion plunger is fit within the insertion tube in engagement with the proximal end of the retraction limiter. The insertion tube is fit through the mastoid opening into the bore hole to engage against the outer surface of the patient cochlea at the cochlear opening. The insertion plunger slides within the insertion tube to push against the proximal end of the retraction limiter to push the electrode array through the cochlear opening into the patient cochlea, and at least a portion of the retraction limiter through the mastoid opening into the middle ear so that when the insertion tube is withdrawn back through the mastoid opening, one or more of the retraction limiting projections enters into the middle ear and displaces out away from the outer surface of the retraction limiter and blocks the mastoid opening so as to prevent retraction of the electrode lead back out from the middle ear.

In further specific embodiments, the method may also include withdrawing and removing the insertion plunger from the insertion tube, disengaging the insertion tube from the outer surface of the patient cochlea, and withdrawing the insertion tube from the bore hole via the mastoid opening.

The retraction limiter may include a plurality of compressible elliptical segments configured to be compressed radially inward to fit within the insertion tube, and configured to expand radially outward when the insertion tube is withdrawn back through the mastoid opening to form the retraction limiting projections. Or the retracting limiting projections may be opposing pairs of flexible flaps.

Embodiments of the present invention also include a cochlear implant system having an electrode arrangement according to any of the foregoing.

DETAILED DESCRIPTION

It appears that the few groups working on developing an insertion mechanism for a minimally invasive cochlear implant electrode array have not yet considered the problem of retracting the insertion device or securely fixing the electrode array prior to retraction of the insertion mechanism. Embodiments of the present invention are directed to a cochlear implant electrode insertion arrangement that resists post-surgical retraction of the inserted electrode back out of the electrode opening. The insertion of the electrode array via the bore hole path is performed with specially designed insertion tools that include an insertion tube for guiding the positioning of the electrode array in front of the cochlear array opening and an insertion plunger to push the array out of the insertion tube into the cochlea.

Figure 1:
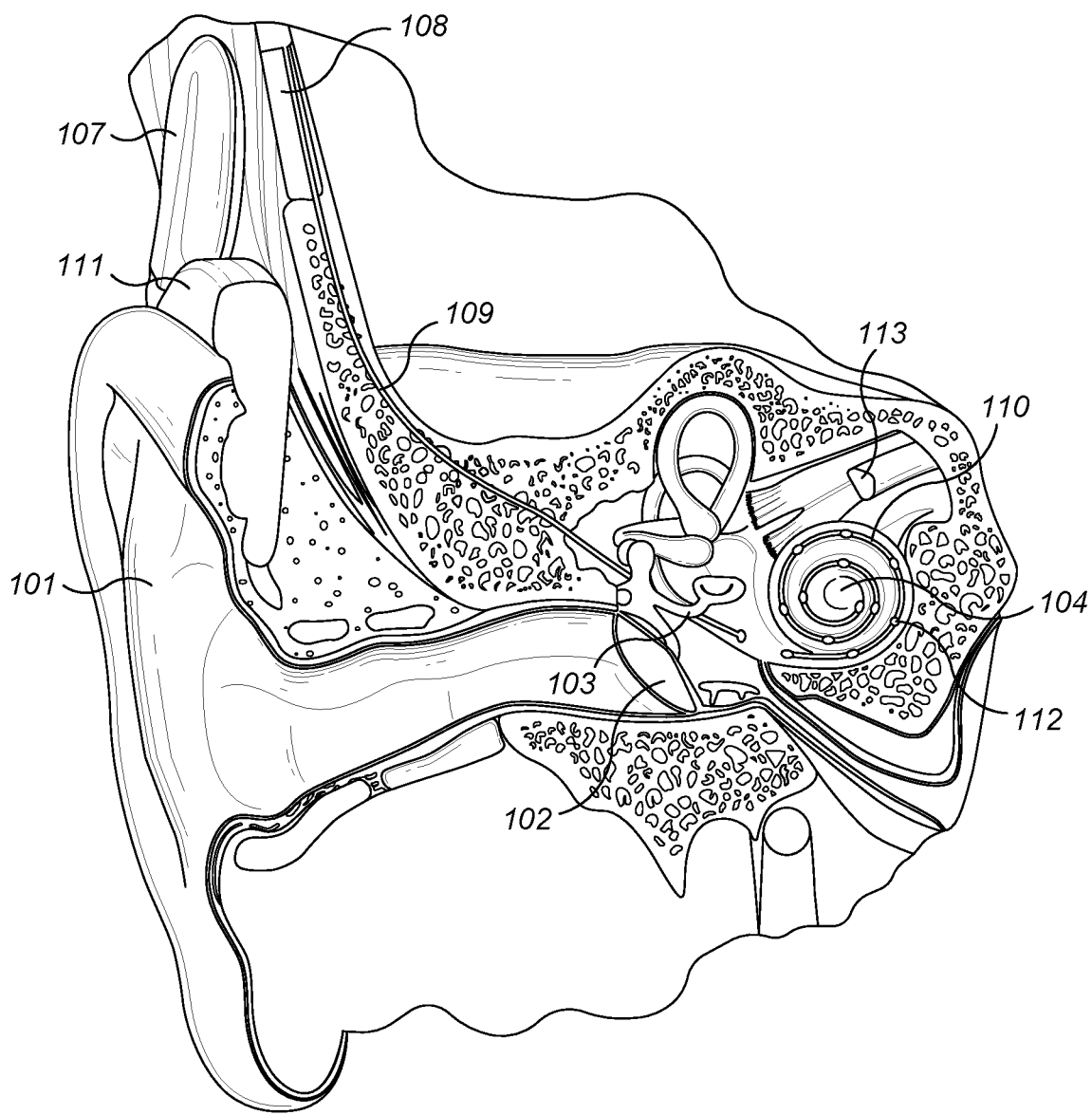
FIG. 1 shows various anatomical structures in a human ear and some components of a typical cochlear implant system.
Figure 2A:
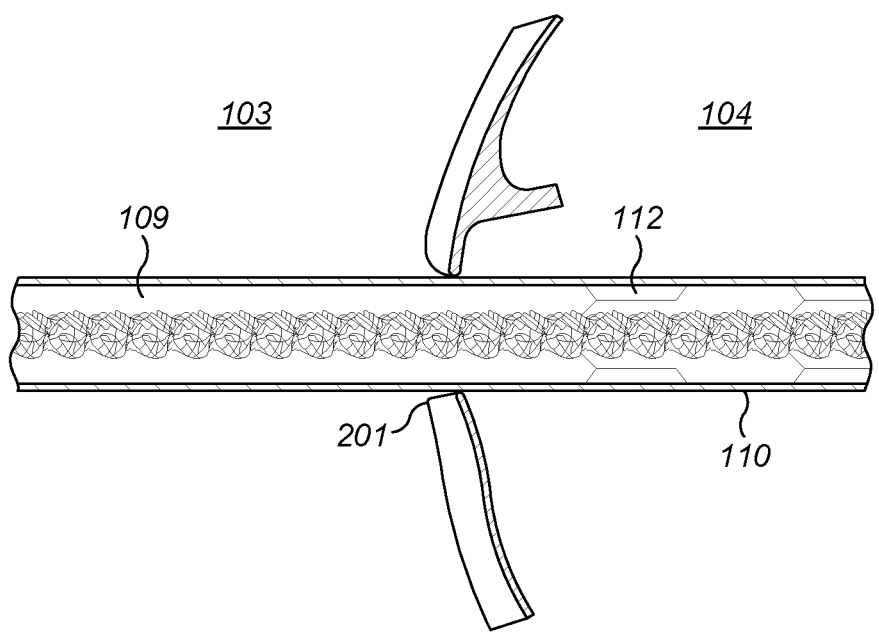
FIG. 2A shows structural details of a cochlear implant electrode arrangement at the electrode opening into the implanted cochlea.
Figure 2B:
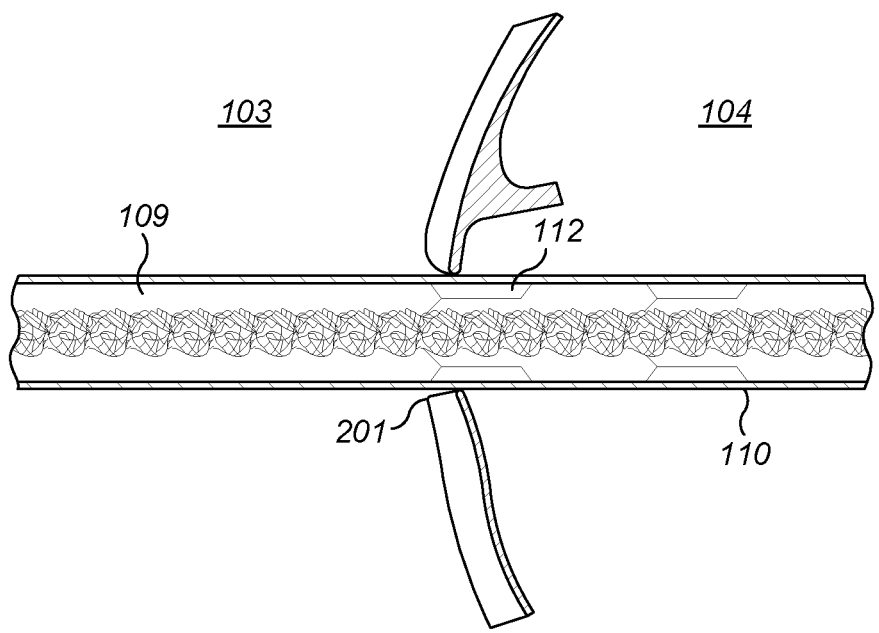
FIG. 2B shows how the proximal end of the intracochlear electrode array can retract back out of the electrode opening to pull the nearest stimulation contact back into the electrode opening.
Figure 3:
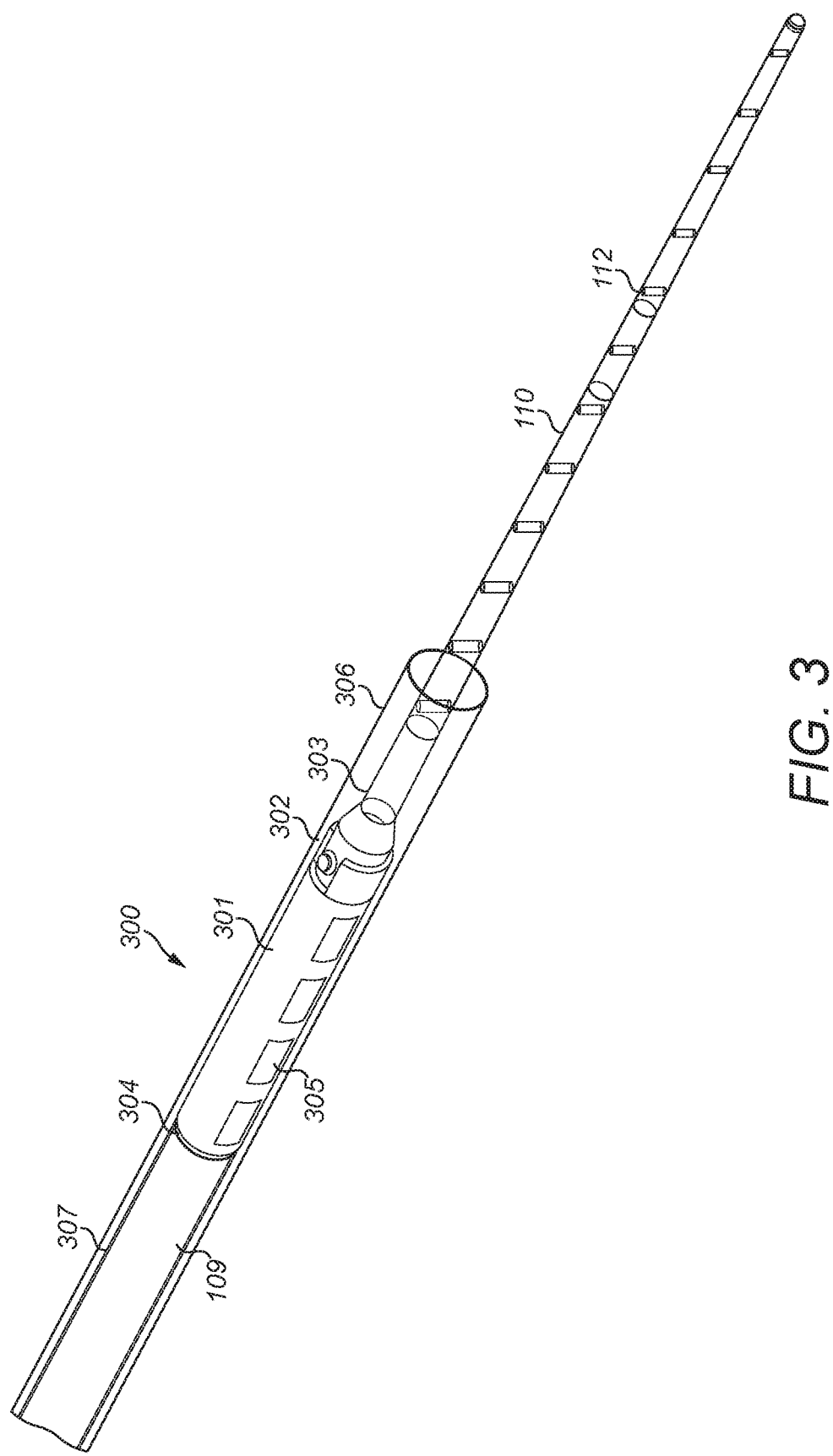
FIG. 3 shows structural details of a portion of an electrode array insertion arrangement with a retraction limiter according to an embodiment of the present invention.

FIG. 3 shows structural details of a portion of an electrode array insertion arrangement with a retraction limiter according to an embodiment of the present invention. An extracochlear electrode lead 109 is configured for carrying one or more cochlear stimulation signals from a proximal end of the electrode lead at a mastoid opening in a patient mastoid bone into the middle ear to a distal end of the electrode lead at a cochlear opening in the outer surface of a patient cochlea 104. An intracochlear electrode array 110 is configured for insertion through the cochlear opening into the patient cochlea 104. The electrode array 110 has a proximal end 303 connected to the distal end of the electrode lead 109, and an outer surface with stimulation contacts 112 configured for applying the cochlear stimulation signals to target neural tissue within the patient cochlea 104.

An insertion mechanism 300 includes a retraction limiter 301 configured to fit around and securely engage a portion of the distal end of the electrode lead 109. The retraction limiter 301 has flexible retraction limiting projections 305 longitudinally distributed along its outer surface between the proximal end 304 of the retraction limiter 301 and the distal end 302 of the retraction limiter 301. An insertion tube 306 is configured to fit around the electrode array 110 and the retraction limiter 301 and engages against the outer surface of the patient cochlea 104 at the cochlear opening. An insertion plunger 307 is configured to fit within the insertion tube 306 and engage against the proximal end 304 of the retraction limiter 301 rather than directly pushing against the electrode array 110.

The insertion mechanism 300 is operable for the insertion plunger 307 to slide within the insertion tube 306 to push against the proximal end 304 of the retraction limiter 301 to push the electrode array 110 through the cochlear opening into the patient cochlea 104, and in one embodiment at least a portion of the retraction limiter 301 through the bore hole toward or into the middle ear 103 so that when the insertion tube 306 is withdrawn back through the mastoid opening, one or more of the retraction limiting projections 305 enters into the bore hole or middle ear 103 and displaces out away from the outer surface of the retraction limiter 301 to block the mastoid opening so as to prevent retraction of the electrode lead 109 back out from the middle ear 103.

Figure 4A:
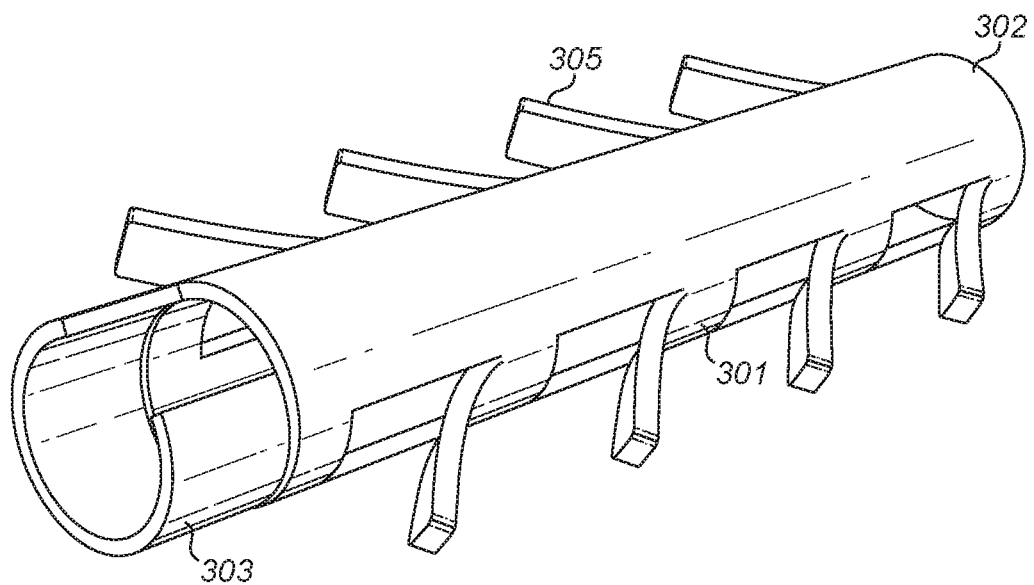
FIGS. 4A and 4B show structural details of the retraction limiter of FIG. 3.
Figure 4B:
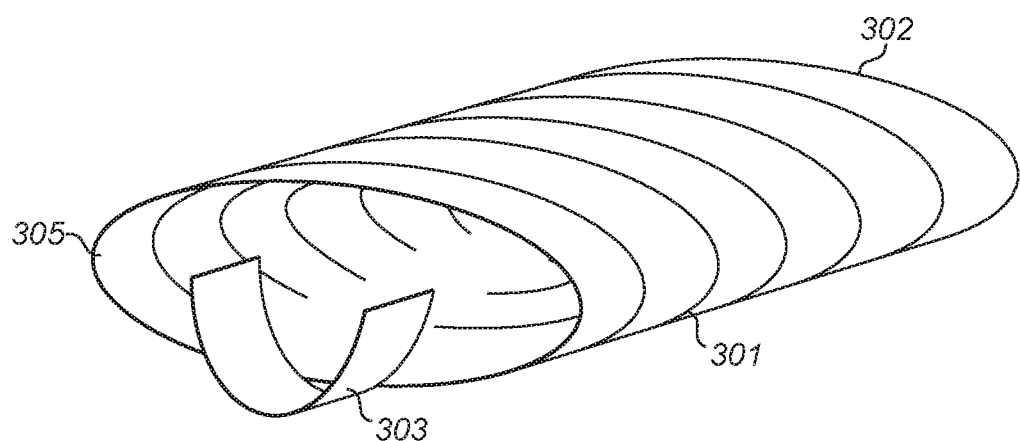

FIGS. 4A and 4B show structural details of the retraction limiter 301 of FIG. 3. Specifically, FIG. 4A shows an embodiment of a retraction limiter 301 where the retracting limiting projections 305 form opposing pairs of flexible flaps. In a more general form, the limiting projections 305 may be equally distributed about the outer surface of the retraction limiter 301 and the number of flexible flaps may vary as well. FIG. 4B shows another embodiment where the retraction limiter 301 is formed of multiple compressible elliptical segments configured to be compressed radially inward to fit within the insertion tube, and configured to expand radially outward when the insertion tube is withdrawn back through the mastoid opening to form the retraction limiting projections 305.

Figure 5:
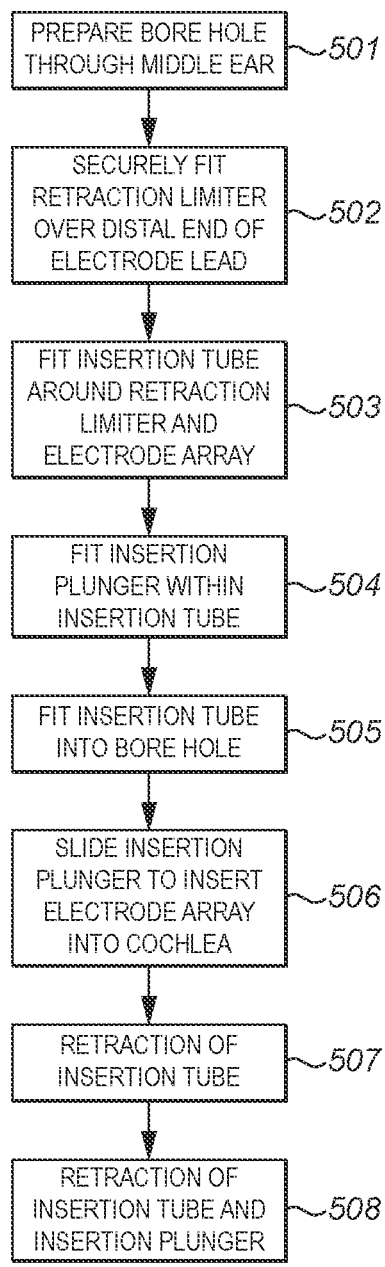
FIG. 5 shows various logical steps in a method of surgically inserting a cochlear implant electrode array according to an embodiment of the present invention.

FIG. 5 shows various logical steps in a method of surgically inserting a cochlear implant electrode array 110 and FIGS. 6A-6D show structural details of the surgical insertion process for a cochlear implant electrode array 110 according to an embodiment of the present invention. First, a bore hole through the middle ear is prepared, step 501, including a mastoid opening 601 through a patient mastoid bone into the middle ear and a cochlear opening 602 through an outer surface of a patient cochlea into the cochlea 104. A retraction limiter 301 structured as described above is securely fit around a distal end of an electrode lead 109 that is configured for carrying one or more cochlear stimulation signals, step 502. An insertion tube 306 is fit around the retraction limiter 301 and an electrode array 110 at the distal end of the electrode lead 109, step 503. An insertion plunger 307 is fit within the insertion tube 306 in engagement with the proximal end of the retraction limiter 301, step 504.

Figure 6A:
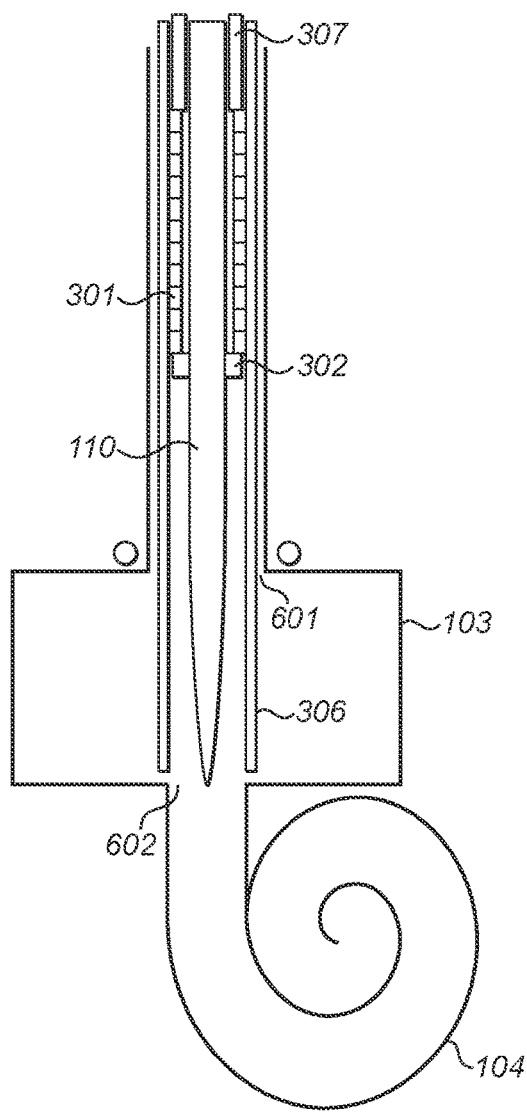
FIGS. 6A-6D show structural details of the surgical insertion process for a cochlear implant electrode according to an embodiment of the present invention.
Figure 6B:
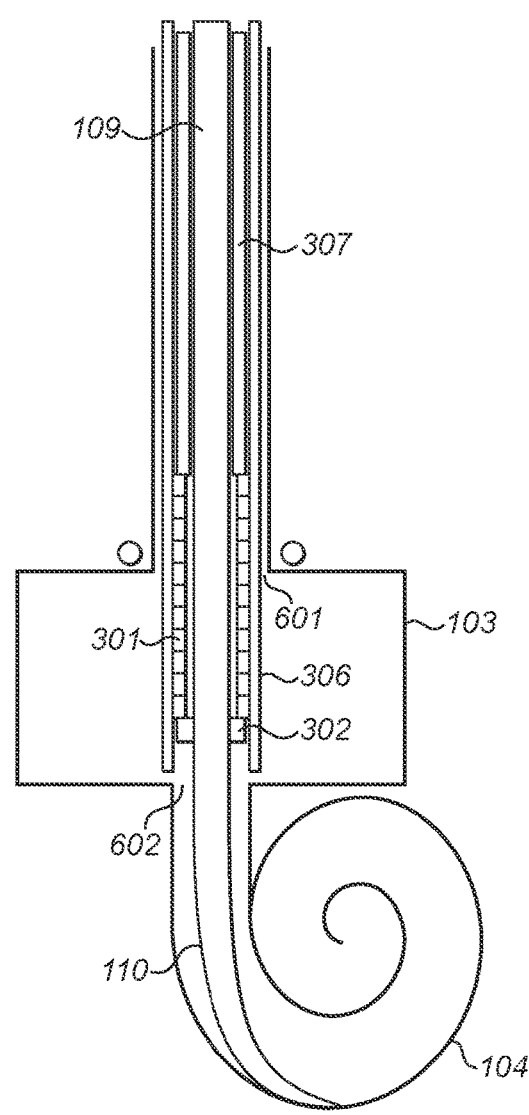
Figure 6C:
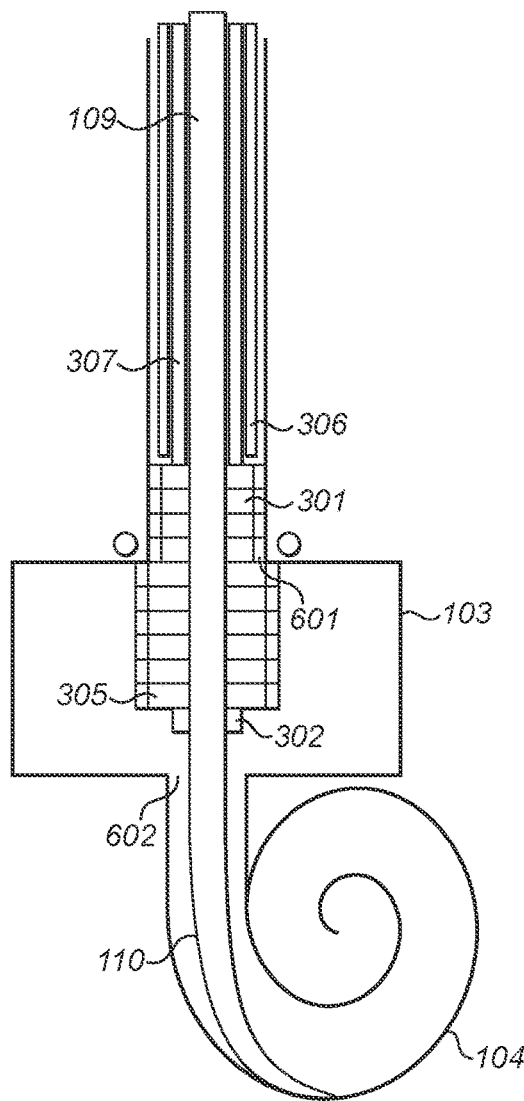
Figure 6D:
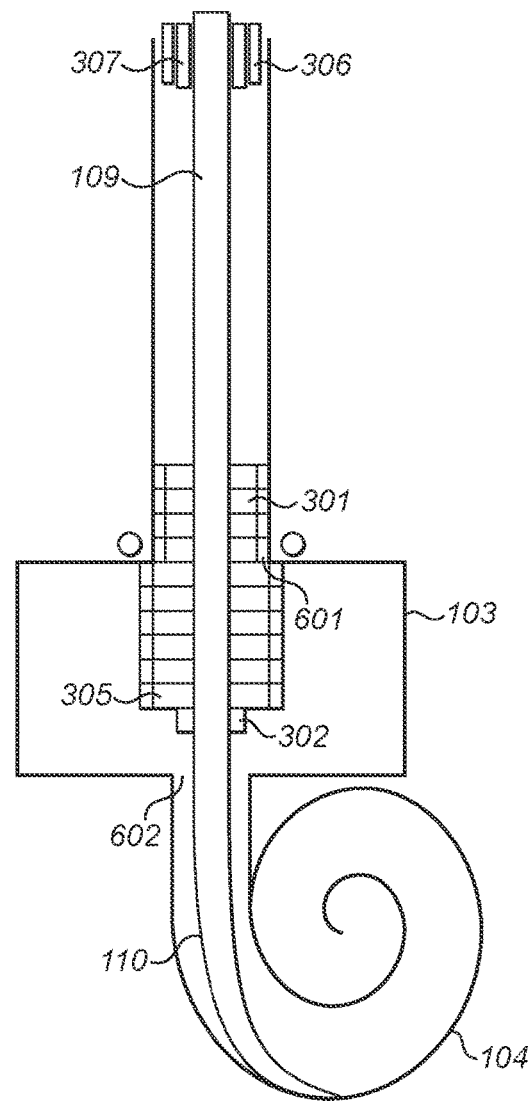

As shown in FIG. 6A, the insertion tube 306 is fit through the mastoid opening 601 into the bore hole, step 505, to engage against the outer surface of the patient cochlea 104 at the cochlear opening 602. The insertion plunger 307 slides within the insertion tube 306 to push against the proximal end of the retraction limiter 301 to push the electrode array 110 through the cochlear opening 602 into the patient cochlea 104, step 506 as shown in FIG. 6B. Subsequently, at step 507, the insertion tube 306 is pulled back with the insertion plunger 307 kept in place to avoid slide-back of the electrode array 110 during retraction of the insertion tube 306. At least a portion of the retraction limiter 301 extends through the bore hole and may in a further embodiment extend through the mastoid opening 601 into the middle ear 103 so that when the insertion tube 306 is withdrawn back through the mastoid opening 601, as shown in FIG. 6C, step 507, one or more of the retraction limiting projections 305 displaces out away from the outer surface of the retraction limiter 301 and blocks the mastoid opening 601 and engages with the bone in the bore hole, and if extended through the mastoid opening 601, enters into the middle ear 103 so as to prevent retraction of the electrode lead 109 back out from the middle ear 103. At step 508, as shown in FIG. 6D, the insertion tube 306 and the insertion plunger 307 are jointly retracted out through the bore hole. Because the limiting projections 305 of retraction limiter already securely fix the electrode array 110, array retraction in this last surgical step is effectively avoided.

One possibility that may eventually arise is a need for explantation of the electrode array, for instance in case of an implant failure. In that case, it may be difficult to withdraw the portion of oval/round embodiment of the retraction limiter shown in FIG. 4A that is positioned inside the middle ear back through the significantly smaller mastoid opening (See FIGS. 6C and 6D), and those blocking retraction limiting projections might even break off as the electrode lead is withdrawn. An embodiment of a retraction limiter where the retraction limiting projections form opposing pairs of flexible flaps as shown in FIG. 4B may be easier to retract in such circumstances.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable electrode arrangement for a cochlear implant system comprising:
   an extracochlear electrode lead configured for carrying one or more cochlear stimulation signals from a proximal end of the electrode lead at a mastoid opening in a patient mastoid bone into the middle ear to a distal end of the electrode lead at a cochlear opening in the outer surface of a patient cochlea;
   an intracochlear electrode array configured for insertion through the cochlear opening into the patient cochlea, the electrode array having a proximal end connected to the distal end of the electrode lead, and an outer surface with a plurality of stimulation contacts configured for applying the cochlear stimulation signals to target neural tissue within the patient cochlea; and
   an insertion mechanism comprising:
   i. a retraction limiter configured to fit around and securely engage a portion of the distal end of the electrode lead, the retraction limiter having a proximal end, a distal end, an outer surface, and a plurality of flexible retraction limiting projections longitudinally distributed along the outer surface of the retraction limiter between the proximal end of the retraction limiter and the distal end of the retraction limiter,
   ii. an insertion tube configured to fit around the electrode array and the retraction limiter and to engage against the outer surface of the patient cochlea at the cochlear opening, and
   iii. an insertion plunger configured to fit within the insertion tube and engage against the proximal end of the retraction limiter;
   wherein the insertion mechanism is operable for the insertion plunger to slide within the insertion tube to push against the proximal end of the retraction limiter to push:
   i. the electrode array through the cochlear opening into the patient cochlea, and
   ii. at least a portion of the retraction limiter through the mastoid opening so that when the insertion tube is withdrawn back through the mastoid opening, one or more of the retraction limiting projections displaces out away from the outer surface of the retraction limiter and blocks the mastoid opening so as to prevent retraction of the electrode lead back out from the middle ear.

2. The electrode arrangement according to claim 1, wherein the retraction limiter comprises a plurality of compressible elliptical segments configured to be compressed radially inward to fit within the insertion tube, and configured to expand radially outward when the insertion tube is withdrawn back through the mastoid opening to form the retraction limiting projections.

3. The electrode arrangement according to claim 1, wherein the retracting limiting projections are opposing pairs of flexible flaps.

4. The electrode arrangement according to claim 1, wherein the insertion mechanism is operable for the insertion plunger to push at least a portion of the retraction limiter into the middle ear so that when the insertion tube is withdrawn back through the mastoid opening, one or more of the retraction limiting projections in the middle ear displaces out away from the outer surface of the retraction limiter into the middle ear and blocks the mastoid opening so as to prevent retraction of the electrode lead back out from the middle ear.

5. A method of implanting an electrode array in a patient cochlea, the method comprising:
   preparing a bore hole including a mastoid opening through a patient mastoid bone into the middle ear and a cochlear opening through an outer surface of a patient cochlea into the cochlea;
   securely fitting a retraction limiter around a distal end of an electrode lead configured for configured for carrying one or more cochlear stimulation signals, the retraction limiter having a proximal end, a distal end, an outer surface, and a plurality of flexible retraction limiting projections longitudinally distributed along the outer surface of the retraction limiter between the proximal end of the retraction limiter and the distal end of the retraction limiter;
   fitting an insertion tube around the retraction limiter and an electrode array having a proximal end connected to the distal end of the electrode lead and an outer surface with a plurality of stimulation contacts configured for applying the cochlear stimulation signals to target neural tissue within an implanted patient cochlea;
   fitting an insertion plunger within the insertion tube in engagement with the proximal end of the retraction limiter;
   fitting the insertion tube through the mastoid opening into the bore hole to engage against the outer surface of the patient cochlea at the cochlear opening;
   sliding the insertion plunger within the insertion tube to push against the proximal end of the retraction limiter to push:
   i. the electrode array through the cochlear opening into the patient cochlea, and
   ii. at least a portion of the retraction limiter through the mastoid opening so that when the insertion tube is withdrawn back through the mastoid opening, one or more of the retraction limiting projections displaces out away from the outer surface of the retraction limiter and blocks the mastoid opening so as to prevent retraction of the electrode lead back out from the middle ear.

6. The method according to claim 5, further comprising:
   withdrawing and removing the insertion plunger from the insertion tube;
   disengaging the insertion tube from the outer surface of the patient cochlea; and
   withdrawing the insertion tube from the bore hole via the mastoid opening.

7. The method according to claim 5, wherein the retraction limiter comprises a plurality of compressible elliptical segments configured to be compressed radially inward to fit within the insertion tube, and configured to expand radially outward when the insertion tube is withdrawn back through the mastoid opening to form the retraction limiting projections.

8. The method according to claim 5, wherein sliding the insertion plunger within the insertion tube includes pushing at least a portion of the retraction limiter through the mastoid opening into the middle ear so that when the insertion tube is withdrawn back through the mastoid opening, one or more of the retraction limiting projections in the middle ear displaces out away from the outer surface of the retraction limiter into the middle ear and blocks the mastoid opening so as to prevent retraction of the electrode lead back out from the middle ear.

9. The method according to claim 5, wherein the retracting limiting projections are opposing pairs of flexible flaps.

\* \* \* \* \*